United States Patent
Ponomarenko et al.

(10) Patent No.: US 8,598,406 B2
(45) Date of Patent: *Dec. 3, 2013

(54) DISPOSABLE ABSORBENT ARTICLE COMPRISING A DURABLE HYDROPHILIC ACQUISITION LAYER

(75) Inventors: Ekaterina Anatolyevna Ponomarenko, Bad Soden am Taunus (DE); John David Carter, Mason, OH (US); Ronald Dean Cramer, Cincinnati, OH (US); Mattias Schmidt, Idstein (DE); Robert Henry Rohrbaugh, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 939 days.

This patent is subject to a terminal disclaimer.

(21) Appl. No.: 11/479,882

(22) Filed: Jun. 30, 2006

(65) Prior Publication Data

US 2006/0247587 A1 Nov. 2, 2006

Related U.S. Application Data

(63) Continuation of application No. 10/758,138, filed on Jan. 15, 2004, now abandoned, and a continuation-in-part of application No. 10/060,708, filed on Jan. 30, 2002, now Pat. No. 7,112,621.

(60) Provisional application No. 60/446,298, filed on Feb. 10, 2003.

(51) Int. Cl.
*A61F 13/53* (2006.01)

(52) U.S. Cl.
USPC .......................................... 604/378; 604/367

(58) Field of Classification Search
None
See application file for complete search history.

(56) References Cited

U.S. PATENT DOCUMENTS

| | | | |
|---|---|---|---|
| 3,381,688 A * | 5/1968 | Satas | 502/407 |
| 3,848,594 A | 11/1974 | Buell | |
| 3,860,003 A | 1/1975 | Buell | |
| 3,862,472 A | 1/1975 | Norton et al. | |
| 3,929,135 A | 12/1975 | Thompson | |
| 3,929,678 A | 12/1975 | Laughlin et al. | |
| 3,982,302 A | 9/1976 | Vaalburg | |
| 4,004,323 A | 1/1977 | Gotchel et al. | |
| 4,057,669 A | 11/1977 | McConnell | |
| 4,097,965 A | 7/1978 | Gotchel et al. | |
| 4,130,915 A | 12/1978 | Gotchel et al. | |
| 4,135,024 A | 1/1979 | Callahan et al. | |
| 4,176,427 A | 12/1979 | Neuenschwander | |
| 4,189,896 A | 2/1980 | Kolbach et al. | |

(Continued)

OTHER PUBLICATIONS

Materials Handbook, Detergents and Alumina, 13th ed. 1991, 5 pages.*

(Continued)

*Primary Examiner* — Susan Su
(74) *Attorney, Agent, or Firm* — Kathleen Y. Carter; John G. Powell; George H. Leal (57) ABSTRACT

A disposable absorbent article having a durable hydrophilic substantially liquid pervious acquisition layer. The acquisition layer includes an acquisition layer substrate and a hydrophilicity boosting composition coated on the acquisition layer substrate. The hydrophilicity boosting composition includes a hydrophilicity boosting amount of nanoparticles having a particle size of from about 1 nanometer to about 750 nanometers.

14 Claims, 6 Drawing Sheets

(56) References Cited

U.S. PATENT DOCUMENTS

| | | | |
|---|---|---|---|
| 4,207,367 A | 6/1980 | Baker, Jr. | |
| 4,296,161 A | 10/1981 | Kaiser et al. | |
| 4,309,469 A | 1/1982 | Varona | |
| 4,463,045 A | 7/1984 | Ahr et al. | |
| 4,468,428 A * | 8/1984 | Early et al. | 428/221 |
| 4,469,746 A * | 9/1984 | Weisman et al. | 442/118 |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,637,859 A | 1/1987 | Trokhan | |
| 4,673,402 A | 6/1987 | Weisman et al. | |
| 4,682,942 A | 7/1987 | Gotchel et al. | |
| 4,695,278 A | 9/1987 | Lawson | |
| 4,699,622 A | 10/1987 | Toussant et al. | |
| 4,795,454 A | 1/1989 | Dragoo | |
| 4,808,178 A | 2/1989 | Aziz et al. | |
| 4,834,735 A | 5/1989 | Alemany et al. | |
| 4,846,815 A | 7/1989 | Scripps | |
| 4,888,231 A | 12/1989 | Angstadt | |
| 4,909,803 A | 3/1990 | Aziz et al. | |
| 4,938,753 A | 7/1990 | Van Gompel et al. | |
| 4,946,527 A | 8/1990 | Battrell | |
| 4,963,140 A | 10/1990 | Robertson et al. | |
| 5,026,364 A | 6/1991 | Robertson | |
| 5,037,416 A | 8/1991 | Allen et al. | |
| 5,093,154 A * | 3/1992 | Hatada et al. | 427/578 |
| 5,151,092 A | 9/1992 | Buell et al. | |
| 5,221,274 A | 6/1993 | Buell et al. | |
| 5,223,096 A | 6/1993 | Phan et al. | |
| 5,240,562 A | 8/1993 | Phan et al. | |
| 5,260,345 A | 11/1993 | DesMarais et al. | |
| 5,269,775 A | 12/1993 | Freeland et al. | |
| 5,342,338 A | 8/1994 | Roe | |
| 5,368,926 A * | 11/1994 | Thompson et al. | 442/239 |
| 5,432,000 A * | 7/1995 | Young et al. | 428/372 |
| 5,451,432 A * | 9/1995 | Lofton | 427/389.9 |
| 5,460,796 A * | 10/1995 | Verduijn | 423/700 |
| 5,518,801 A | 5/1996 | Chappell et al. | |
| 5,554,145 A | 9/1996 | Roe et al. | |
| 5,556,509 A | 9/1996 | Trokhan et al. | |
| 5,569,234 A | 10/1996 | Buell et al. | |
| 5,571,096 A | 11/1996 | Dobrin et al. | |
| 5,576,282 A | 11/1996 | Miracle et al. | |
| 5,580,411 A | 12/1996 | Nease et al. | |
| 5,580,423 A | 12/1996 | Ampulski et al. | |
| 5,582,644 A * | 12/1996 | Gaddis et al. | 118/303 |
| 5,591,152 A | 1/1997 | Buell et al. | |
| 5,607,760 A | 3/1997 | Roe | |
| 5,609,587 A | 3/1997 | Roe | |
| 5,614,574 A * | 3/1997 | Sheth | 524/140 |
| 5,635,191 A | 6/1997 | Roe et al. | |
| 5,643,588 A | 7/1997 | Roe et al. | |
| 5,650,222 A | 7/1997 | DesMarais et al. | |
| 5,669,897 A | 9/1997 | Lavon et al. | |
| 5,707,950 A | 1/1998 | Kasturi et al. | |
| 5,865,823 A | 2/1999 | Curro | |
| 5,922,161 A * | 7/1999 | Wu et al. | 156/272.6 |
| 5,938,648 A | 8/1999 | Lavon et al. | |
| 5,968,025 A | 10/1999 | Roe et al. | |
| 6,004,306 A | 12/1999 | Robles et al. | |
| 6,201,056 B1 * | 3/2001 | Zhu | 524/493 |
| 6,296,737 B1 * | 10/2001 | Wu et al. | 162/164.1 |
| 6,398,768 B1 * | 6/2002 | Palumbo et al. | 604/355 |
| 6,645,569 B2 | 11/2003 | Cramer et al. | |
| 6,863,933 B2 | 3/2005 | Cramer et al. | |
| 7,112,621 B2 | 9/2006 | Rohrbaugh et al. | |
| 2003/0148684 A1 | 8/2003 | Cramer et al. | |
| 2004/0052957 A1 * | 3/2004 | Cramer et al. | 427/421 |
| 2004/0158212 A1 | 8/2004 | Ponomarenko et al. | |
| 2004/0158213 A1 | 8/2004 | Ponomarenko et al. | |
| 2004/0158214 A1 | 8/2004 | Ponomarenko et al. | |
| 2005/0008839 A1 * | 1/2005 | Cramer et al. | 428/221 |
| 2006/0247587 A1 * | 11/2006 | Ponomarenko et al. | 604/360 |
| 2006/0253092 A1 * | 11/2006 | Ponomarenko et al. | 604/360 |
| 2006/0258999 A1 * | 11/2006 | Ponomarenko et al. | 604/360 |

OTHER PUBLICATIONS

U.S. Appl. No. 11/480,194, filed Jun. 30, 2006, Ponomarenko et al.
U.S. Appl. No. 11/479,545, filed Jun. 30, 2006, Ponomarenko et al.

* cited by examiner

DISPOSABLE ABSORBENT ARTICLE COMPRISING A DURABLE HYDROPHILIC ACQUISITION LAYER

CROSS REFERENCE TO RELATED APPLICATIONS

This application is a continuation of U.S. application Ser. No. 10/758,138 filed on Jan. 15, 2004 now abandoned, which claims the benefit of U.S. Provisional Application No. 60/446,298, filed Feb. 10, 2003, and this application is a continuation in part of U.S. application Ser. No. 10/060,708 filed on Jan. 30, 2002 now U.S. Pat. No. 7,112,621.

FIELD OF THE INVENTION

The present invention relates to disposable absorbent article comprising a durable hydrophilic acquisition layer, and methods of producing same.

BACKGROUND OF THE INVENTION

Disposable absorbent articles such as diapers and adult incontinence products are well known in the art. Such disposable articles collect and retain urine and fecal material deposited thereon by the wearer.

Nonwoven fabrics made of synthetic fibers and/or natural fibers are commonly used in absorbent articles, for example, as topsheet material or as acquisition layers. Such nonwoven fabrics are usually hydrophobic. However, for many applications in hygiene products it is necessary to have hydrophilic nonwoven. Therefore the nonwoven fabric has to be treated accordingly.

A common method for rendering nonwoven fabrics hydrophilic is coating the surface of the nonwoven with hydrophilic surfactants. As this coating does not lead to a tight chemical bond between the nonwoven and the surfactant, the surfactant can be washed off during use when the absorbent article is wetted. The decrease in liquid strike-through time is a desirable effect when the nonwoven is coated with surfactant. Liquid strike-through refers to liquid passing through the nonwoven fabric with liquid strike-through time referring to the time it takes for a certain amount of liquid to pass through the nonwoven. However, as the surfactant is washed off when coated nonwoven fabrics are exposed to the liquid, the strike-through time in the next gushes is increased. This results in performance reduction during use on diapers or other articles comprising such nonwoven fabrics. Furthermore, at the same time as liquid strike-through time decreases due to use of surfactants, surface tension of the liquid, which was in contact with the nonwoven fabric, is reduced. This reduction is undesirable, because it can cause increased urine leakage in a diaper.

Another common method to render a nonwoven fabric hydrophilic is by applying corona and/or plasma treatment. Plasma is an ionized form of gas that can be obtained by ionizing a gas or liquid medium. Plasmas are widely used for the treatment of organic and inorganic materials to promote adhesion between various materials. Polymers that have chemically inert surfaces with low surface energies do not allow good coatings with bondings and adhesives. Thus, these surfaces are treated to make them receptive to bonding with other substrates, coatings, adhesives and printing inks.

However, corona and plasma treatments lead to low coating durability upon storage of the treated material, i.e., hydrophilicity decreases over time.

Thus, there is a need for a hydrophilic coating of a nonwoven, which is durable upon storage, is not easily washed off when wetted and allows the nonwoven to achieve fast liquid strike-through in multiple exposures to liquid.

It should be understood that every limit given throughout this specification will include every lower or higher limit, as the case may be, as if such lower or higher limit was expressly written herein. Every range given throughout this specification will include every narrower range that falls within such broader range, as if such narrower ranges were all expressly written herein.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawing wherein:

DETAILED DESCRIPTION OF THE INVENTION

The term "coating", as used herein, includes coatings that completely cover a surface, or portion thereof (e.g., continuous coatings, including those that form films on the surface), as well as coatings that may only partially cover a surface, such as those coatings that after drying leave gaps in coverage on a surface (e.g., discontinuous coatings). The later category of coatings may include, but is not limited to, a network of covered and uncovered portions and distributions of nanoparticles on a surface which may have spaces between the nanoparticles. In some embodiments, the coating preferably forms at least one layer of nanoparticles on the surface which has been coated, and is substantially uniform. However, when the coatings described herein are described as being applied to a surface, it is understood that the coatings need not be applied to, or that they cover the entire surface. For instance, the coatings will be considered as being applied to a surface even if they are only applied to modify a portion of the surface.

The term "hydrophilic" describes fibers or surfaces of fibers, which are wettable by aqueous fluids (e.g., aqueous body fluids) deposited on these fibers. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A fiber or surface of a fiber is said to be wetted by a fluid (i.e., hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

As used herein, the term "hydrophilicity boosting" means a composition when coated on a topsheet substrate to make a durable, hydrophilic substantially liquid pervious topsheet, produces a durable, hydrophilic substantially liquid pervious topsheet which has a liquid Strike-Through time for the first gush of less than or equal to about 6 seconds, more preferably less than or equal to about 4 seconds, and has a liquid Strike-Through time for the fifth gush of test liquid, of preferably less than or equal to about 6 seconds, more preferably less than or equal to about 4 seconds, when tested in accordance with the Strike-Through Test in the Test Methods section and further described herein.

As used herein, the term "comprising" means that the various components, ingredients, or steps can be conjointly employed in practicing the present invention. Accordingly, the term "comprising" is open-ended and encompasses the more restrictive terms "consisting essentially of" and "consisting of".

The disposable absorbent articles of the present invention comprise an absorbent core which comprises a durable hydrophilic fluid pervious acquisition layer. Examples of illustrative disposable absorbent articles, include but are not limited to, diapers, adult incontinence products, training pant, feminine hygiene pads, panty liners and the like. The durable hydrophilic fluid pervious acquisition layer comprises an acquisition layer substrate which has been coated with a hydrophilicity boosting composition. The substrate and hydrophilicity boosting composition are both exemplified in more detail herein.

Figure 1:
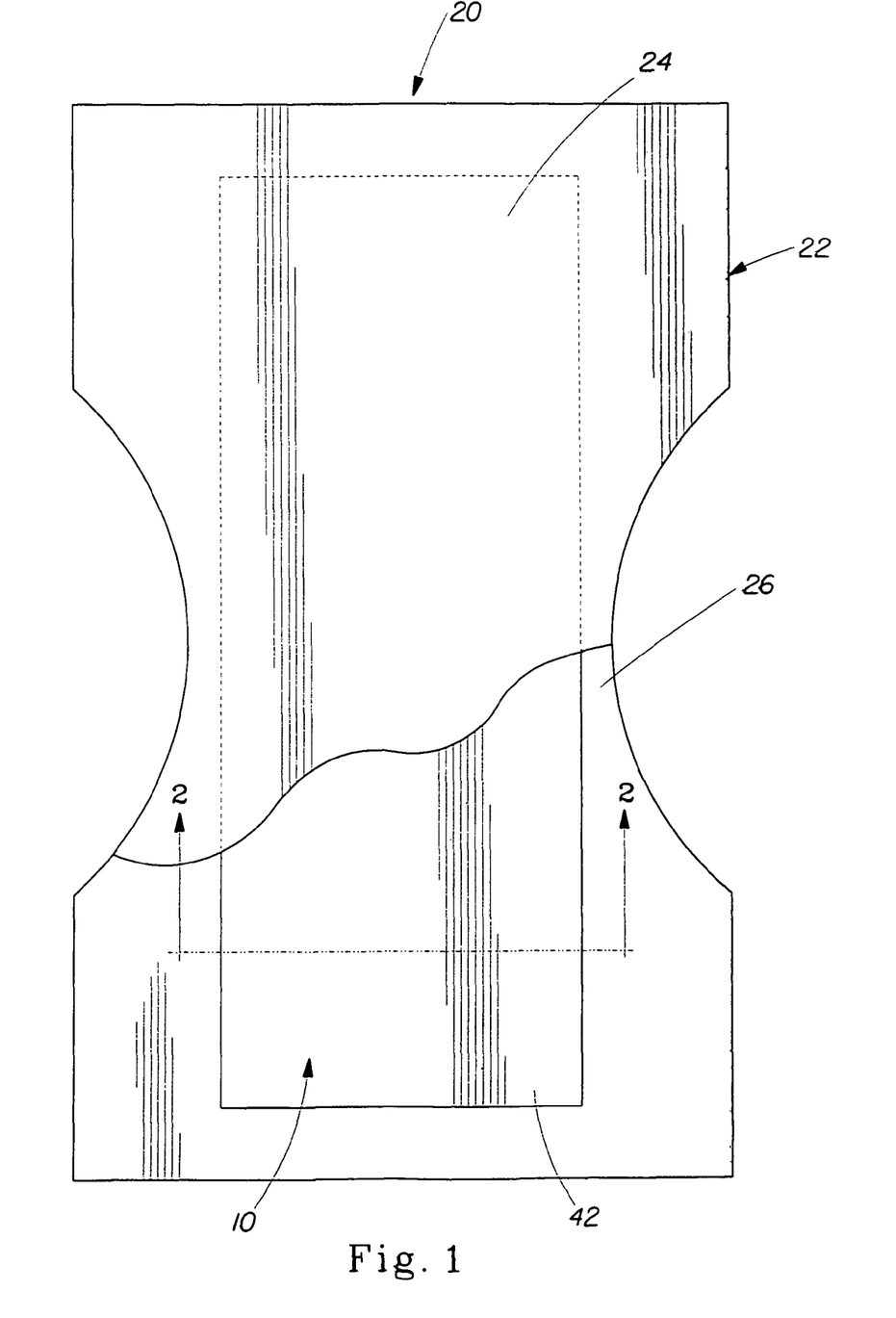
FIG. 1 is a partial cut-away top plan view of a disposable absorbent article according to the present invention.

FIG. 1 is a plan view of a disposable absorbent article, specifically a diaper 20, which is a preferred embodiment of an absorbent article according to the present invention. The diaper is shown in its flat out, uncontracted state (i.e., without elastic induced contraction). Portions of the structure are cut away to show the underlying structure of the diaper 20, especially the absorbent core 10. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most or all of the absorbent core 10 encased between the topsheet 24 and the backsheet 26. The absorbent core 10 in FIG. 1 generally is disposed between the topsheet 24 and the backsheet 26.

For unitary absorbent articles, the chassis 22 comprises the main structure of the diaper with other features added to form the composite diaper structure. While the topsheet 24, the backsheet 26, and the absorbent core 10 may be assembled in a variety of well-known configurations, preferred diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 10. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 10 between the backsheet 26 and the topsheet 24. The backsheet 26 may be joined with the topsheet 24. The backsheet 26 prevents the exudates absorbed by the absorbent core 10 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097.

Diapers 20 according to the present invention may be provided with a re-closable fastening system (not shown) or may alternatively be provided in the form of pant-type diapers.

The diaper 20 may also include such other features (not shown) as are known in the art including front and rear ear panels, re-closable fastening system, lotion, waist cap features, pant type diapers, elastics and the like to provide better fit, containment and aesthetic characteristics. Additional illustrative, but non-limiting, information on construction, assembly, and the various components of disposable diapers may be found in U.S. Pat. No. 3,860,003 to Buell; U.S. Pat. No. 5,151,092 to Buell; U.S. Pat. No. 5,221,274 to Buell; U.S. Pat. No. 5,554,145 to Roe et al. on Sep. 10, 1996; U.S. Pat. No. 5,569,234 to Buell et al.; U.S. Pat. No. 5,580,411 to Nease et al.; U.S. Pat. No. 6,004,306 to Robles et al.; U.S. Pat. No. 5,938,648 to LaVon et al.; U.S. Pat. No. 5,865,823 to Curro; U.S. Pat. No. 5,571,096 to Dobrin et al.; U.S. Pat. No. 5,518,801 to Chappell, et al.; U.S. Pat. No. 4,573,986 to Minetola et al.; U.S. Pat. No. 3,929,135, to Thompson; U.S. Pat. No. 4,463,045 to Ahr, et al.; U.S. Pat. No. 4,609,518 to Curro et al.; U.S. Pat. No. 4,629,643 to Curro et al.; U.S. Pat. No. 5,037,416 to Allen et al.; U.S. Pat. No. 5,269,775 to Freeland et al.; U.S. Pat. No. 4,610,678 to Weisman et al.; U.S. Pat. No. 4,673,402 to Weisman et al.; U.S. Pat. No. 4,888,231 to Angstadt; U.S. Pat. No. 5,342,338 to Roe; U.S. Pat. No. 5,260,345 to DesMarais et al.; U.S. Pat. No. 5,026,364 to Robertson; U.S. Pat. No. 3,848,594 to Buell; U.S. Pat. No. 4,846,815 to Scripps; U.S. Pat. No. 4,946,527 to Battrell; U.S. Pat. No. 4,963,140 to Robertson et al.; U.S. Pat. No. 4,699,622 to Toussant et al.; U.S. Pat. No. 5,591,152 to Buell et al.; U.S. Pat. No. 4,938,753 to Van Gompel, et al.; U.S. Pat. No. 5,669,897 to LaVon, et al.; U.S. Pat. No. 4,808,178 to Aziz et al.; U.S. Pat. No. 4,909,803 to Aziz et al.: U.S. Pat. No. 4,695,278 to Lawson; U.S. Pat. No. 4,795,454 issued to Dragoo; U.S. Pat. No. 5,607,760 to Roe on; U.S. Pat. No. 5,609,587 to Roe; U.S. Pat. No. 5,635,191 to Roe et al.; U.S. Pat. No. 5,643,588 to Roe et al.; and U.S. Pat. No. 5,968,025 to Roe et al.

Figure 2:
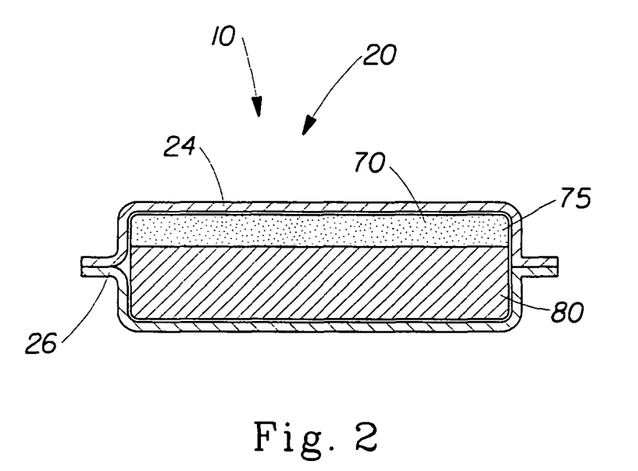
FIG. 2 is a sectional view along 2-2 of one alternative embodiment of the disposable absorbent article of FIG. 1.

The absorbent core 10 comprises a durable hydrophilic acquisition layer 70 and a storage layer 80 as shown in FIG. 2. The storage layer 80 may comprise any absorbent material that is generally compressible, conformable, non-irritating to the wearer's skin, and capable of absorbing and retaining liquids such as urine and other certain body exudates. The storage layer 80 may comprise a wide variety of liquid-absorbent materials commonly used in disposable diapers and other absorbent articles such as comminuted wood pulp, which is generally referred to as air felt or fluff. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (such as superabsorbent fibers), absorbent gelling materials, or any other known absorbent material or combinations of materials. Examples of some combinations of suitable absorbent materials are fluff with absorbent gelling materials and/or superabsorbent polymers, and absorbent gelling materials and superabsorbent fibers etc. The storage layer may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997.

FIG. 2 is a sectional view along 2-2 showing a section of one alternative embodiment of the absorbent core 10 of the diaper of FIG. 1. In FIG. 2 the absorbent core 10 comprises durable hydrophilic acquisition layer 70. The durable hydrophilic acquisition layer 70 comprises a substrate which has been coated with a hydrophilicity boosting composition which contains nanoparticles 75. The substrate may be a nonwoven, a polymeric film or combinations thereof. In one optional embodiment of the acquisition layer 70 comprises a substrate which is a nonwoven fabric whereas the storage layer 80 preferably comprises a mixture of chemically stiffened, twisted and curled fibers, high surface area fibers and thermoplastic binding fibers. In another preferred embodiment both the acquisition and storage layers 70 and 80 are provided from a non-woven material, which is preferably hydrophilic. The acquisition layer 70 preferably is in direct contact with the storage layer. The substrate, hydrophilicity boosting composition, the nonwoven, and the porous polymeric film are all exemplified in more detail herein.

The durable hydrophilic acquisition layer of the present invention provides a substrate which has both an extended shelf life and wear life. Prior high-energy treatments tended to have a short shelf life. That is, during the time from purchase to ultimate use and disposal by the consumer the substrate would trend to loose its hydrophilicity. Surfactant treatments, such as those of the prior art, on the other hand would often have an adequate shelf life, but have an inadequate wear life. That is, upon contact with bodily fluids, such as urine, the substrate would instantly being to loose its hydrophilic properties. This may even lead to a surface which repels the bodily fluids it is designed to absorb even though the absorbent article has not reached its total absorbance capacity.

The durable hydrophilic acquisition layer of the present invention suffers neither of these limitations as the substrates treated with the hydrophilicity boosting composition of the present invention have a long shelf life and long wear life, that is the hydrophilic properties of the core wrap are not substantially lost over time or upon contact with bodily fluids such as urine.

In one optional embodiment of the present invention the durable hydrophilic acquisition layer has a wash-off surface tension of greater than about 65 mN/m, when tested in accordance with the Determination of Surface Tension Test in the Test Methods section and further described herein.

In one optional embodiment of the present invention the durable hydrophilic acquisition layer is a carded resin bonded PET nonwoven material, or an air laid nonwoven material containing a portion or patch of PET. Theses terms and materials are both exemplified in more detail herein.

Figure 3:
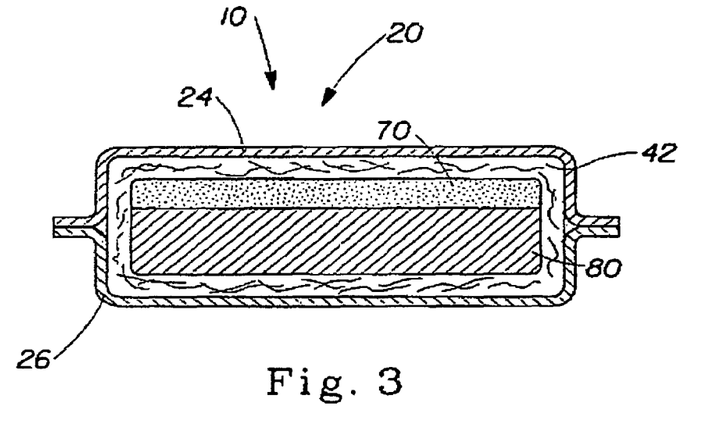
FIG. 3 is a sectional view along 2-2 of another alternative embodiment of the disposable absorbent article of FIG. 1.

FIG. 3 is a sectional view along 2-2 showing an embodiment of the diaper 20 of FIG. 1. In FIG. 3 the storage layer 80 and acquisition layer 70 are surrounded or enveloped by a core wrap 42. The core wrap 42 comprises a substrate, such as a nonwoven, material, film and combinations thereof. In one optional embodiment of the present invention, the core wrap 42 may be coated with a hydrophilicity boosting composition, which is exemplified in more detail herein.

Acquisition Layer Substrate—

The durable hydrophilic acquisition layer of the present invention comprises an acquisition layer substrate (substrate) which has been coated with a hydrophilicity boosting composition. The substrate of interest herein may comprise any known type of substrate, including but not limited to fabrics, garments, textiles, and films. In certain embodiments, the substrate may comprise one or more fibers. A fiber is defined as a fine hairlike structure, of animal, vegetable, mineral, or synthetic origin. Commercially available fibers have diameters ranging from less than about 0.001 mm (about 0.00004 in) to more than about 0.2 mm (about 0.008 in) and they come in several different forms: short fibers (known as staple, or chopped), continuous single fibers (filaments or monofilaments), untwisted bundles of continuous filaments (tow), and twisted bundles of continuous filaments (yarn).

The substrate may comprise fibers made by nature (natural fibers), made by man (synthetic or man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Synthetic fibers can be derived from natural fibers or not. For example synthetic fibers which are derived from natural fibers, include but are not limited to, rayon and lyocell, both of which are derived from cellulose. Synthetic fibers which are not derived from natural fibers can be derived from other natural sources or from mineral sources. Exemplary synthetic fibers derived from natural sources, include but are not limited to, polysaccharides such as starch. Exemplary fibers from mineral sources, include but are not limited to, polyolefin fibers such as polypropylene and polyethylene fibers, which are derived from petroleum, and silicate fibers such as glass and asbestos. Synthetic fibers are commonly formed, when possible, by fluid handling processes (e.g., extruding, drawing, or spinning a fluid such as a resin or a solution). Synthetic fibers are also formed by solid handling size reduction processes (e.g., mechanical chopping or cutting of a larger object such as a monolith, a film, or a fabric).

Examples of suitable synthetic fibers which may comprise all or part of the substrates of the present invention include but are not limited, to nylon (polyamide), acrylic (polyacrylonitrile), aramid (aromatic polyamide), polyolefin (polyethylene and polypropylene), polyester, polyethylene terepthalate (PET), butadiene-styrene block copolymers, natural rubber, latex, spandex (polyurethane) and combinations thereof.

Synthetic fibers that contain more than one type of repeat unit can result from combining repeat units at the molecular level within each macromolecular strand (co-polymer), between macromolecular strands (homopolymer blends), or combinations thereof (co-polymer blends); or they can result from combining repeat units at a higher scale level with distinct nanoscopic, microscopic, or macroscopic phases (e.g., multicomponent fibers). Each component of a multi-component fiber can comprise a homopolymer, a co-polymer, or blends thereof. Bicomponent fibers are common versions of multicomponent fibers. The two or more types of repeat units in a copolymer can be arranged randomly or in alternating blocks of each type. Blocks of different types of repeat units can joined to one another at their respective ends (block co-polymers) or between the respective end of at least one block (graft co-polymers).

Nonwoven materials are a type of fabric typically made from fibers in a web format. Nonwoven materials are described by Butler I, Batra S K, et al, *Nonwovens Fabrics Handbook*, Association of the Nonwoven Fabrics Industry, 1999, and by Vaughn E A, *Nonwoven Fabric Sampler and Technology Reference*, Association of the Nonwoven Fabrics Industry.

Substrates comprising nonwoven materials can be formed by direct extrusion processes during which the fibers and the nonwoven materials are formed at about the same point in time, or by preformed fibers which can be laid into nonwoven materials at a distinctly subsequent point in time. Exemplary direct extrusion processes include but are not limited to: spunbonding, meltblowing, solvent spinning, electrospinning, and combinations thereof typically forming layers. Exemplary "laying" processes include wetlaying and drylaying. Example drylaying processes include but are not limited to airlaying, carding, and combinations thereof typically forming layers. Combinations of the above processes yield nonwovens commonly called hybrids or composites. Exemplary combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at the about the same point in time as the direct extrusion process (e.g., spinform and coform for SA and MA), or at a subsequent point in time. In the above examples, one or more individual layers can be created by each process. For instance, SMS can mean a three layer, 'sms' nonwoven materials, a five layer 'ssmms' nonwoven materials, or any reasonable variation thereof wherein the lower case letters designate individual layers and the upper case letters designate the compilation of similar, adjacent layers.

The fibers in a nonwoven material are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof.

Fibers and nonwoven materials can be subjected to additional treatment after formation. For nonwoven materials, additional treatment commonly occurs after the fibers are joined to one another (post-treatment). Examples of additional treatments include but are not limited to mechanical stresses, chemical additives, or combinations thereof.

It is also within the scope of the present invention that the term "acquisition layer substrate" includes laminates of two or more substrates or webs. Commercially available laminates, or purpose built ones would also be within the scope of the present invention. Additionally, the substrates may be flat or textured. The formation of textured substrates and laminates forms no part of this invention. The following discussion is for convenience of formulation, but is not intended to limit the type of substrate used herein.

In one optional embodiment of the present invention the substrate is treated with a high-energy surface treatment. This high-energy treatment may be prior to or concurrent with the coating of the substrate with the hydrophilicity boosting composition. The high-energy treatment may be any suitable high-energy treatment for increasing the hydrophilicity of a substrate. Suitable high-energy treatments, include but are not limited to, corona discharge treatment, plasma treatment, UV radiation, ion beam treatment, electron beam treatment and combinations thereof.

High-energy surface treatments which increase surface energy are useful in that in combination with the nanoparticles they can provide the surface with durable hydrophilic properties. In turn, increased surface energy increases the wettability of the substrate without use of surfactants in the dispersion to achieve wetting. Avoiding use of surfactant is useful for reasons previously discussed. In a non-limiting example, corona treatment places transient charges on fibrous thermoplastic surfaces. As discussed earlier, partial or full charges dissipate over time, and maintaining partial or full charges on fibrous thermoplastic surfaces is a common limitation. However, it has been found that corona treatment in combination with the nanoparticles can be used to place a durable charge on the material so that water continues to be attracted to the material after time elapses. The use of nanoparticles in conjunction with high-energy surface treatments, can convert the transient properties of such treatments to more durable properties. In a non-limiting example, corona treatment of a 13 gram per square meter hydrophobic SMS polypropylene nonwoven subsequently treated with a hydrophilicity boosting compositions and dried exhibited consistently fast strikethrough following multiple gushes or insults. Without wishing to be bound by theory, the corona treatment increased the surface energy for the fiber. The hydrophilicity boosting compositions without a surfactant was brought into contact with the fiber surfaces before the charges could dissipate. The higher surface energy enabled the dispersion to wet the fibrous surfaces better than would have been possible without the corona treatment. On the surfaces which are wetted, the nanoparticles associate with the partial or full charge on the surface which would otherwise be transient. This association may take the form of a van der Waals interaction or the form of some other interaction or bond. The nanoparticles are sufficiently small to render the associations sufficient strong to withstand multiple strikethroughs. The nanoparticle is sufficiently large to resist rotation away from oxygen into the polymer or dissipate in general.

Additional illustrative, but non limiting, information on mechanical entanglement and by chemical bonding of fiber, as well as additional treatments to nonwoven material, such as high-energy treatment, may be found in copending US Published Patent Application No. 2002/0151634 (application Ser. No. 10/060,708) filed on Jan. 30, 2002, published on Oct. 17, 2002; US Published Patent Application No. 2002/0192366 (application Ser. No. 10/060,694) filed on Jan. 30, 2002, published on Dec. 19, 2002; US Published Patent Application No. 2002/0150678 (application Ser. No. 10/060,582) filed on Jan. 30, 2002, published on Oct. 17, 2002; U.S. patent application Ser. No. 10/338,603 filed on Jan. 8, 2003; and U.S. patent application Ser. No. 10/338,610 filed on Jan. 8, 2003.

The following patents may referred to for their disclosures related to the substrate: U.S. Pat. No. 3,862,472 issued Jan. 28, 1975; U.S. Pat. No. 3,982,302 issued Sep. 28, 1976; U.S. Pat. No. 4,004,323 issued Jan. 25, 1977; U.S. Pat. No. 4,057,669 issued Nov. 8, 1977; U.S. Pat. No. 4,097,965 issued Jul. 4, 1978; U.S. Pat. No. 4,176,427 issued Dec. 4, 1979; U.S. Pat. No. 4,130,915 issued Dec. 26, 1978; U.S. Pat. No. 4,135,024 issued Jan. 16, 1979; U.S. Pat. No. 4,189,896 issued Feb. 26, 1980; U.S. Pat. No. 4,207,367 issued Jun. 10, 1980; U.S. Pat. No. 4,296,161 issued Oct. 20, 1981; U.S. Pat. No. 4,309,469 issued Jan. 25, 1982; U.S. Pat. No. 4,682,942 issued Jul. 28, 1987; and U.S. Pat. Nos. 4,637,859; 5,223,096; 5,240,562; 5,556,509; and 5,580,423.

Hydrophilicity Boosting Composition—The hydrophilicity boosting compositions of the present invention comprise a hydrophilicity boosting amount of nanoparticles. By hydrophilicity boosting amount, it is intended that an amount of nanoparticles be present in the hydrophilicity boosting compositions which are sufficient to make a substrate to which it is applied more hydrophilic. Such amounts are readily ascertained by one of ordinary skill in the art and are based on many factors, including but not limited to, the substrate used, the nanoparticles used, the desired hydrophilicity of the durable hydrophilic acquisition layer, the consumer product in which the absorbent core is used, etc. Preferably the nanoparticles are present in the hydrophilicity boosting compositions at levels of from about 0.0001% to about 20%, preferably from about 0.001% to about 15%, and more preferably from about 0.001% to about 10%, by weight of the composition.

Typically the amount of hydrophilicity boosting compositions present on a substrate will vary depending upon many factors, including but not limited to, the substrate used, the nanoparticles used, the desired hydrophilicity of the durable hydrophilic acquisition layer, the consumer product in which the absorbent core is used, etc. Preferably, the amount of hydrophilicity boosting compositions on the substrate will be between about 0.01 grams of hydrophilicity boosting composition per square meter of substrate (or gsm substrate) and about 30 gsm substrate, more preferably between about 0.01 gsm substrate and about 20 gsm substrate, even more preferably between about 0.1 gsm substrate and about 10 gsm substrate. In one preferred embodiment of the present invention the nanoparticles are applied to the substrate as a dispersion in a carrier.

Nanoparticles are particles which have a particle size, that is diameter, which is of the order of magnitude of nanometers. That is, nanoparticles have a particle size ranging from about 1 to about 750 nanometers. Such particles are technologically significant since they are utilized to produce durable hydrophilic acquisition layer that have novel and useful properties due to the very small dimensions of their particulate constituents. Nanoparticles with particle sizes ranging from about 2 nm to about 750 nm can be economically produced. Non-limiting examples of particle size distributions of the nanoparticles are those that fall within the range from about 2 nm to less than about 750 nm, alternatively from about 2 nm to less than about 200 nm, and alternatively from about 2 nm to less than about 150 nm.

The particle size of the nanoparticles is the largest diameter of a nanoparticle The mean particle size of various types of nanoparticles may differ from the particle size distribution of the nanoparticles particles. For example, a layered synthetic silicate can have a mean particle size of about 25 nanometers while its particle size distribution can generally vary between about 10 nm to about 40 nm. (It should be understood that the particle sizes that are described herein are for particles when they are dispersed in an aqueous medium and the mean particle size is based on the mean of the particle number distribution. Non-limiting examples of nanoparticles can include crystalline or amorphous particles with a particle size from about 2 to about 750 nanometers. Boehmite alumina can have an average particle size distribution from 2 to 750 nm.)

When the hydrophilicity boosting composition is present on the substrate it will typically be a substantially uniform coating. When the hydrophilicity boosting composition dries, for example any water evaporates, the nanoparticles may aggregate together on the substrate forming larger particles, or even appear film like, depending upon the observation method used. In any event, the application of a hydrophilicity boosting composition comprising nanoparticles, provides for a uniform coat of the substrate.

Either organic or inorganic nanoparticles may be used in the hydrophilicity boosting composition of the present invention. Suitable organic nanoparticles include, but are not limited to, nanolatexes. A "nanolatex", as used herein, is a latex with particle sizes less than or equal to about 750 nm. A "latex" is a colloidal dispersion of water-insoluble polymer particles that are usually spherical in shape. Nanolatexes may be formed by emulsion polymerization. "Emulsion polymerization" is a process in which monomers of the latex are dispersed in water using a surfactant to form a stable emulsion followed by polymerization. Particles thus produced can range in size from about 2 to about 600 nm.

While organic nanoparticles are within the scope of the present invention, inorganic nanoparticles are preferred. Inorganic nanoparticles generally exist as oxides, silicates, carbonates and hydroxides. Some layered clay minerals and inorganic metal oxides can be examples of nanoparticles. The layered clay minerals suitable for use in the present invention include those in the geological classes of the smectites, the kaolins, the illites, the chlorites, the attapulgites and the mixed layer clays. Typical examples of specific clays belonging to these classes are the smectices, kaolins, illites, chlorites, attapulgites and mixed layer clays. Smectites, for example, include montmorillonite, bentonite, pyrophyllite, hectorite, saponite, sauconite, nontronite, talc, beidellite, volchonskoite and vermiculite. Kaolins include kaolinite, dickite, nacrite, antigorite, anauxite, halloysite, indellite and chrysotile. Illites include bravaisite, muscovite, paragonite, phlogopite and biotite. Chlorites include corrensite, penninite, donbassite, sudoite, pennine and clinochlore. Attapulgites include sepiolite and polygorskyte. Mixed layer clays include allevardite and vermiculitebiotite. Variants and isomorphic substitutions of these layered clay minerals offer unique applications.

Layered clay minerals may be either naturally occurring or synthetic. An example of one non-limiting embodiment of the coating composition uses natural or synthetic hectorites, montmorillonites and bentonites. Another embodiment uses the hectorites clays commercially available, and typical sources of commercial hectorites are the LAPONITEs from Southern Clay Products, Inc., U.S.A; VEEGUM PRO and VEEGUM F from R. T. Vanderbilt, U.S.A.; and the Barasyms, Macaloids and PROPALOIDs from Baroid Division, National Read Comp., U.S.A.

In one preferred embodiment of the present invention the nanoparticles comprise a synthetic hectorite such as a lithium magnesium silicate. One such suitable lithium magnesium silicate is LAPONITE, which has the formula:

wherein w=3 to 6, x=0 to 3, y=0 to 4, z=12−2w−x, and the overall negative lattice charge is balanced by counter-ions;

and wherein the counter-ions are selected from the group consisting of selected $Na^+$, $K^+$, $NH_4^+$, $Cs^+$, $Li^+$, $Mg^{++}$, $Ca^{++}$, $Ba^{++}$, $N(CH_3)_4^+$ and mixtures thereof. (If the LAPONITE is "modified" with a cationic organic compound, then the "counter-ion" could be viewed as being any cationic organic group (R)).

Other suitable synthetic hectorites include, but are not limited to isomorphous substitutions of LAPONITE, such as, LAPONITE B, LAPONITE S, LAPONITE XLS, LAPONITE RD, LAPONITE XLG, and LAPONITE RDS.

The nanoparticles may also be other inorganic materials, including inorganic oxides such as, but not limited to, titanium oxide silica, zirconium oxide, aluminum oxide, magnesium oxide and combinations thereof. Other suitable inorganic oxides include various inorganic oxides of alumina and silica.

In one preferred embodiment of the present invention the nanoparticles comprise a Boehmite alumina ($[Al(O)(OH)]_n$) which is a water dispersible, inorganic metal oxide that can be prepared to have a variety of particle sizes or range of particle sizes, including a mean particle size distribution from about 2 nm to less than or equal to about 750 nm. For example, a boehmite alumina nanoparticle with a mean particle size distribution of around 25 nm under the trade name Disperal P2™ and a nanoparticle with a mean particle size distribution of around 140 nm under the trade name of Dispal® 14N4-25 are available from North American Sasol, Inc.

Use of mixtures of nanoparticles in the hydrophilicity boosting compositions is also within the scope of the present invention.

In one preferred embodiment of the present invention the nanoparticles are selected from the group consisting of titanium dioxide, Boehmite alumina, sodium magnesium lithium fluorosilicates and combinations thereof.

Optional Ingredients—

The hydrophilicity boosting compositions of the present invention may also include optional ingredients such as a carrier, surfactant and adjunct ingredients.

Optional ingredients, when present, are typically employed in compositions at levels of from about 0.001% to about 99.9%, preferably from about 0.01% to about 98%, and more preferably from about 0.1% to about 96%, by weight of the composition.

Suitable carriers include liquids, solids and gases. One preferred carrier is water, which can be distilled, deionized, or tap water. Water is valuable due to its low cost, availability, safety, and compatibility.

Optionally, in addition to or in place of water, the carrier can comprise a low molecular weight organic solvent. Preferably, the solvent is highly soluble in water, e.g., ethanol, methanol, acetone, ethylene glycol, propanol, isopropanol, and the like, and mixtures thereof. Low molecular weight alcohols can reduce the surface tension of the nanoparticle dispersion to improve wettability of the substrate. This is particularly helpful when the substrate is hydrophobic. Low molecular weight alcohols can also help the treated substrate to dry faster. The optional water soluble low molecular weight solvent can be used at any suitable level. The carrier can comprise any suitable amount of the composition, including but not limited to from about 10% to about 99%, alternatively from about 30% to about 95%, by weight of the coating composition.

Surfactants are an optional ingredient in some embodiments of the present invention. Surfactants are especially useful in the coating composition as wetting agents to facilitate the dispersion of nanoparticles onto the substrate. Surfactants are preferably included when the coating composition is used to treat a hydrophobic substrate.

Suitable surfactants can be selected from the group including anionic surfactants, cationic surfactants, nonionic surfactants, amphoteric surfactants, ampholytic surfactants, zwitterionic surfactants and mixtures thereof. Nonlimiting examples of surfactants useful in the compositions of the present invention are disclosed in McCutcheon's, *Detergents and Emulsifiers*, North American edition (1986), published by Allured Publishing Corporation; McCutcheon's, *Functional Materials*, North American Edition (1992); U.S. Pat. Nos. 5,707,950 and 5,576,282; and U.S. Pat. No. 3,929,678, to Laughlin et al., issued Dec. 30, 1975.

When a surfactant is used in the coating composition, it may be added at an effective amount to provide facilitate application of the coating composition. Surfactant, when present, is typically employed in compositions at levels of from about 0.0001% to about 60%, preferably from about 0.001% to about 35%, and more preferably from about 0.001% to about 25%, by weight of the composition.

Nonlimiting examples of surfactants, including preferred nonionic surfactants, useful herein typically at levels from about 0.001% to about 60%, by weight, include nonionic and amphoteric surfactants such as the $C_{12}$-$C_{18}$ alkyl ethoxylates ("AE") including the so-called narrow peaked alkyl ethoxylates and $C_6$-$C_{12}$ alkyl phenol alkoxylates (especially ethoxylates and mixed ethoxy/propoxy), $C_{12}$-$C_{18}$ betaines and sulfobetaines ("sultaines"), $C_{10}$-$C_{18}$ amine oxides, and the like.

Another class of useful surfactants is silicone surfactants and/or silicones. They can be used alone and/or alternatively in combination with the alkyl ethoxylate surfactants described herein. Nonlimiting examples of silicone surfactants are the polyalkylene oxide polysiloxanes having a dimethyl polysiloxane hydrophobic moiety and one or more hydrophilic polyalkylene side chains, and having the general formula:

wherein a+b are from about 1 to about 50, and each $R^1$ is the same or different and is selected from the group consisting of methyl and a poly(ethyleneoxide/propyleneoxide) copolymer group having the general formula: —$(CH_2)_nO(C_2H_4O)_c$ $(C_3H_6O)_dR^2$, wherein n is 3 or 4; total c (for all polyalkyleneoxy side groups) has a value of from 1 to about 100, alternatively from about 6 to about 100; total d is from 0 to about 14; alternatively d is 0; total c+d has a value of from about 5 to about 150, alternatively from about 9 to about 100 and each $R^2$ is the same or different and is selected from the group consisting of hydrogen, an alkyl having 1 to 4 carbon atoms, and an acetyl group, alternatively hydrogen and methyl group. Each polyalkylene oxide polysiloxane has at least one $R^1$ group being a poly(ethyleneoxide/propyleneoxide) copolymer group. Silicone superwetting agents are available from Dow Corning as silicone glycol copolymers (e.g., Q2-5211 and Q2-5212).

It is also within the scope of the present invention to use a mixture of surfactants.

Adjunct ingredients—

The compositions can contain other optional adjunct ingredients, including but not limited to process aids, antimicrobial preservatives, antioxidants, anti-static agents, chelating agents, colorants, dyes, filler salts, fungicides, insect and moth repellant agents, germicides, hydrotropes, metallic salts. These optional ingredients may be included at any desired level, but are typically added at a level of from about 0.0001% to about 99.99% by weight of the composition.

Applying the hydrophilicity boosting composition to the substrate—

The hydrophilicity boosting composition can be applied to the substrate in any suitable manner. The hydrophilicity boosting composition can be applied to the substrate when the substrate is at least partially immersed in a bath of the composition (immersive processes), or without immersing the substrate in the coating composition (non-immersive processes).

In one embodiment of the present invention the hydrophilicity boosting composition is applied by kiss-roll coating. In kiss-roll coating, the composition is kept in a suitable bath. A rotating cylinder or any other device suitable for this process, is contacting the composition with at least a part of its surface. Thus, the composition is spread on the surface of the cylinder. The substrate is brought into contact with the cylinder while the cylinder already has the composition spread on its surface. In this process, the amount of composition applied on the substrate can be controlled easily and it is possible to avoid soaking the substrate with composition.

Alternatively to the kiss-roll coating, the composition can also be sprayed on the surface of the plurality of fibers. Like the kiss-roll coating, spraying enables low and easily controllable add-on level of aqueous solution, which is preferred in the present invention. Other alternative methods include, but are not limited to, printing such as, rotary, gravure, flexographic printing, ink jet printing, slot coating and the like.

EXAMPLES

Hydrophilicity boosting compositions, according to the present invention, are prepared as follows:

correct height. Precision of test should be +/−0.1 mN/m. Procedure (i) Calibration: Pour 40 ml of saline (0.9 wt % NaCl in deionized water) into a cleaned beaker. Test the surface tension of the saline with a platinum ring or a platinum plate using the method described in equipment instructions. The surface tension should be 71-72 mN/m at 20° C. (ii) Method: Clean the beaker with deionized water and isopropanol, including burning it out with a gas burner for a few seconds. Wait until the beaker temperature equilibrates to room temperature is reached. Place ten 60×60 mm pieces of test nonwoven into a cleaned beaker. The nonwoven should have a basis weight of at least 10 grams per square meter (or gsm). Add 40 ml of saline (0.9 wt % NaCl in deionized water) and stir by hand with a clean surfactant-free plastic stick for 10 seconds. Let the solution with nonwoven stand for 5 minutes. Stir again by hand for ten seconds. Remove the nonwovens from the saline with a clean surfactant-free plastic stick. Let the solution stand for ten minutes. Then test the liquids surface tension with a platinum plate or platinum ring; using the method described in the equipment instructions. The measured surface tension is the wash-off surface tension.

Liquid Strike-Through Test—The liquid strike-through time is measured using Lister-type strike-through equipment, manufactured by Lenzing AG, Austria. Test procedure is based on standardized EDANA (European Disposables And Nonwovens Association) method 150.3-96, with the test sample placed on an absorbent pad comprised of ten plies of filter paper (Ahlstrom Grade 632 obtained from Empirical Manufacturing Co., Inc., or equivalent). In a typical experiment, three consecutive 5 ml gushes of test liquid (0.9% saline solution) are applied to a nonwoven sample at one

|  | % Wt of Component | | | | | | | | | | | | |
|---|---|---|---|---|---|---|---|---|---|---|---|---|---|
| Component | 1 | 2 | 3 | 4 | 5 | 6 | 7 | 8 | 9 | 10 | 11 | 12 | 13 |
| Nanoparticle[1] | 0.1 | 0.05 | 0.05 | | | | | 0.1 | 1 | | | | |
| Nanoparticle[2] | | | | 0.1 | 0.05 | 0.05 | 0.1 | | | | | | |
| Nanoparticle[3] | | | | | | | | | | 1 | 1 | 4 | |
| Nanoparticle[4] | | | | | | | | | | | | | 1 |
| Surfactant[5] | 0.075 | 0.075 | | 0.075 | 0.075 | | | | | | 0.075 | 0.075 | |
| Surfactant[6] | | | 0.025 | | | 0.025 | | | | | | | |
| Water | quantity sufficient to 100% | | | | | | | | | | | | |

[1]LAPONITE B is sodium magnesium lithium fluorosilicate from Southern Clay Products, Inc.
[2]LAPONITE RD is sodium magnesium lithium silicate from Southern Clay Products, Inc.
[3]DISPERAL 14N4-25 is a boehmite alumina nanoparticle available from North American Sasol, Inc
[4]ZSM5 is a nanosized zeolite with a particle size from 70 to about 400 nm.
[5]NEODOL 91-6
[6]SILWET L-77

Test Methods—Unless otherwise stated, all tests are performed under standard laboratory conditions (50% humidity and at 73° F. (23° C.)).

Contact Angle—Dynamic contact angles are measured using the FTA200 Dynamic Contact Angle Analyzer, made by First Ten Angstroms, USA. A single drop of test solution is dispensed onto the sample substrate. A digital video recording is made while the drop spreads out across the surface of the substrate and the FTA200 software measures the contact angle of the liquid with the substrate as a function of time.

Determination of surface tension—The surface tension (unit: mN/m) is determined according to the following test. Apparatus: Equipment: K10 tensiometer provided by Krüss GmbH, Germany or equivalent. The vessel elevation speed should be 4 mm/min. Liquid surface height should be sensed automatically when using a plate or a ring. The equipment must be able to adjust the sample position automatically to the minute intervals and the respective strike-through times are recorded without changing the absorbent pad.

In addition to measuring the strike-through time for the first gush, as described in the Edana Method, the test described below does not only measure the first gush but several subsequent gushes, especially the fifth gush.

Figure 4:
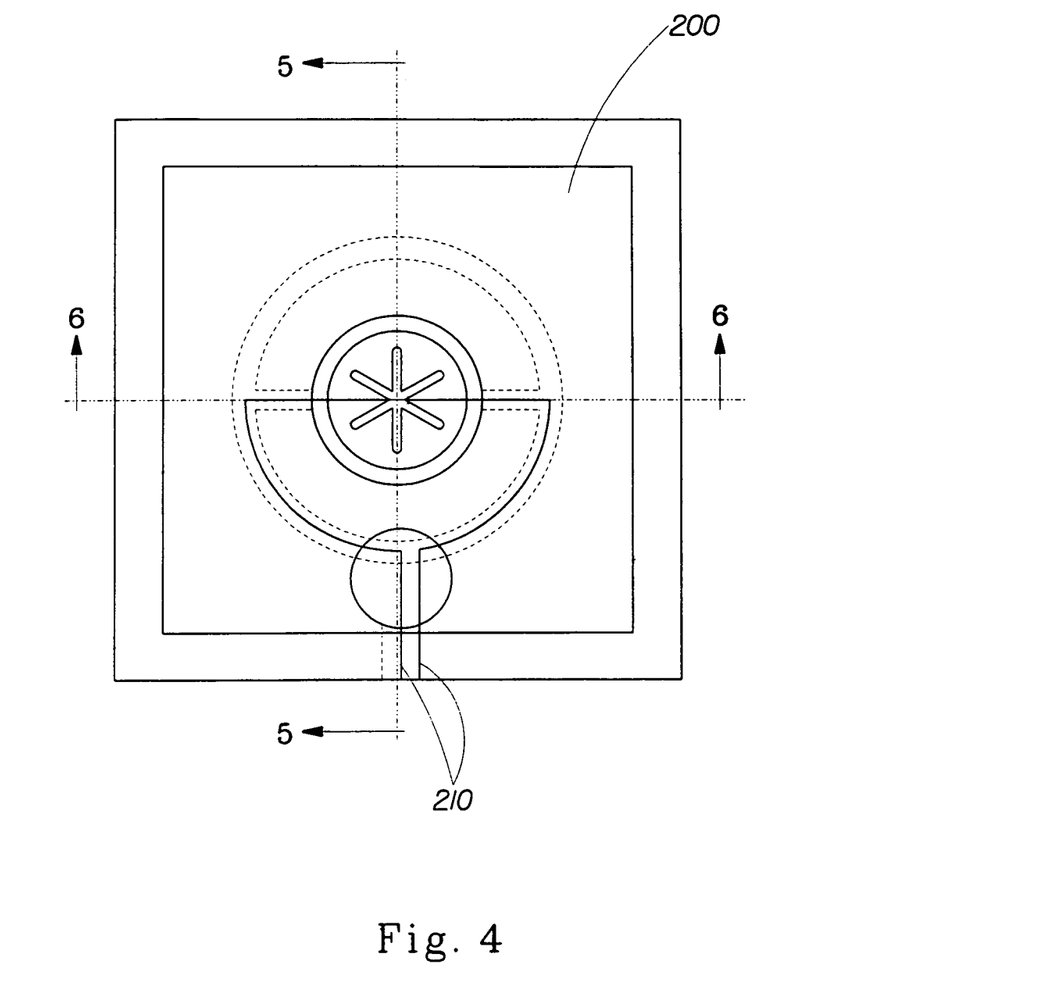
FIG. 4 is a schematic top view of a strike-through plate which may be used to measure Liquid Strike-through of a substrate.
Figure 5:
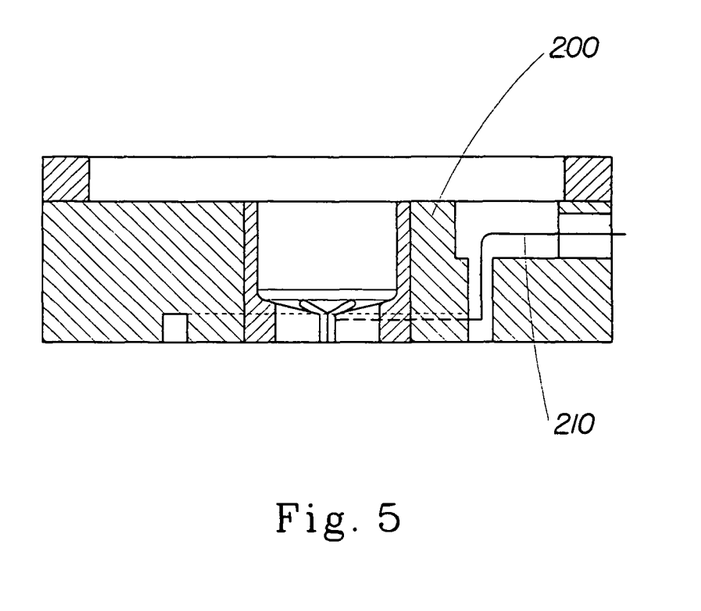
FIG. 5 is a sectional view along 5-5 of the strike-through plate of FIG. 4.
Figure 6:
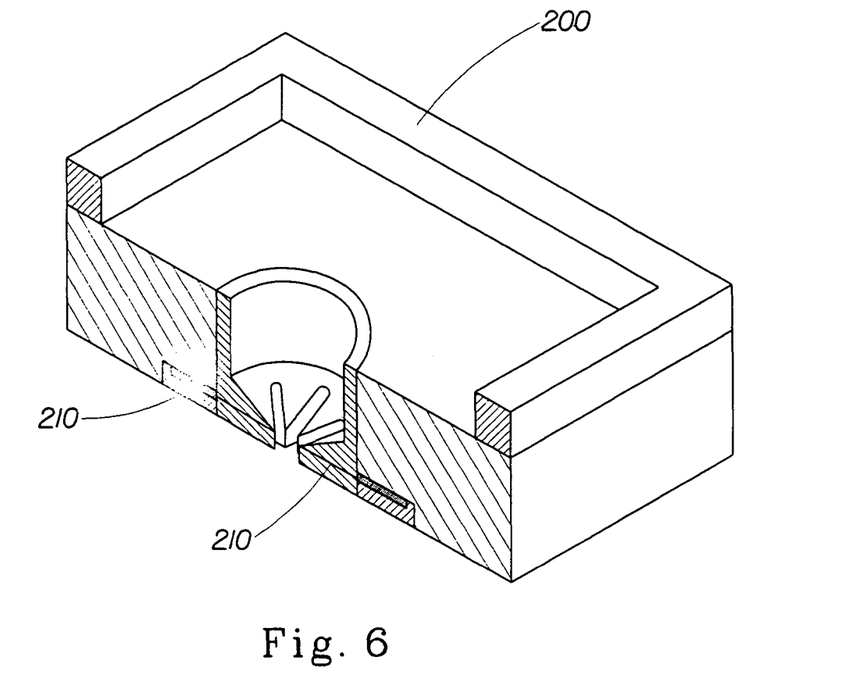
FIG. 6 is a sectional perspective view along 6-6 of the strike-through plate of FIG. 4.

Apparatus—Lister Strike-through Equipment—(i) A Funnel fitted with magnetic valve: Rate of discharge of 25 ml in 3.5 (±0.25) seconds; (ii) A Strike-Through plate: Constructed of 25 mm thick acrylic glass. The total weight of the plate must be 500 g. The electrodes should be of non-corrosive material. The electrodes are set in (4.0 mm×7.0 mm) cross section grooves, cut in the base of the plate and fixed with quick setting epoxy resin. FIGS. 4, 5, and 6 illustrate a Strike-Through plate 200 containing electrodes 210. FIG. 4 is a top view of a Strike-Through plate 200, where as FIG. 5 is a sectional view along 5-5 of the Strike-Through plate 200 of FIG. 4. FIG. 6 is a sectional perspective view along 6-6 of the Strike-Through plate 200 of FIG. 4; (iii) Base plate: A square of acrylic glass 125 mm×125 mm approximately; (iv) Ring stand to support the funnel; (v) Electronic Timer measuring to 0.01 seconds; (vi) Burette with 50 ml capacity; and (vii) Core filter paper Ahlström Grade 989 or equivalent (average Strike-Through time 1.7 s+−0.3 s, dimensions: 10×10 cm).

Procedure: (1) Carefully cut the required number of samples, 12.5 cm×12.5 cm with touching the sample only at the edge of the sample. (2) Taking 10 plies of Core filter paper place one sample on the set of 10 plies of filter paper on the base plate. The sample should be positioned on the filter paper in such a way that the side of the nonwoven, which is intended to face the user's skin (when applied in an absorbent article) is uppermost. (3) Place the Strike-Through plate on top with the center of the plate over the center of the test piece. Center the burette and the funnel over the plate. (4) Ensuring that the electrodes are connected to the timer, switch on the timer and set the clock to zero. (5) Fill the burette with saline solution (0.9 wt % NaCl in deionized water). (6) Keep the discharge valve of the funnel closed and run 5.0 ml of liquid (=one gush) from the burette into the funnel. (7) Open the magnetic valve of the funnel to discharge 5.0 ml of liquid. The initial flow of liquid will complete the electrical circuit and start the timer. It will stop when the liquid has penetrated into the pad and fallen below the level of the electrodes in the Strike-Through plate. (8) Record the time indicated on the electronic timer. (9) Wait 60 seconds and repeat steps (4), and (6) to (9) for the second, the third gush and any subsequent gush, with each gush comprising 5 ml of liquid. (e.g., 5 ml into funnel, open magnetic valve, etc.) Record the Time for the 1st, 2nd and any subsequent gush in seconds.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. All percentages, ratios and proportions are by weight, and all temperatures are in degrees Celsius (° C.), unless otherwise specified. All measurements are in SI units, unless otherwise specified.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising a topsheet, a backsheet and an absorbent core disposed therebetween, said absorbent core comprising a durable, hydrophilic fluid pervious acquisition layer and a storage layer said storage layer being disposed between said acquisition layer and said backsheet, said acquisition layer comprising:
    (a) a nonwoven acquisition layer substrate formed from a plurality of hydrophobic fibers selected from the group consisting of polyolefin fibers, polyester fibers, and combinations thereof; and
    (b) a hydrophilicity boosting composition coated on said substrate, said hydrophilicity boosting composition comprising a surfactant and a hydrophilicity boosting amount of nanoparticles, wherein said nanoparticles have a particle size of from about 1 to about 750 nanometers; and wherein the surfactant is present in an amount to facilitate dispersion of the nanoparticles onto the substrate.

2. The disposable absorbent article according to claim 1 wherein said nonwoven material comprises fibers selected from the group consisting of polypropylene, polyethylene, polyethylene terephthalate, rayon and combinations thereof.

3. The disposable absorbent article according to claim 1 wherein said nanoparticles are inorganic nanoparticles.

4. The disposable absorbent article according to claim 3 wherein said nanoparticles are selected from the group consisting of titanium dioxide, layered clay minerals, alumina oxide, silicates, and combinations thereof.

5. The disposable absorbent article according to claim 4 wherein said nanoparticles are selected from the group consisting of titanium dioxide, Boehmite alumina, sodium magnesium lithium fluorosilicates and combinations thereof.

6. The disposable absorbent article according to claim 1 wherein said surfactant is a nonionic surfactant.

7. The disposable absorbent article according to claim 1 wherein said disposable absorbent article is selected from the group consisting of diapers, adult incontinence products, training pant, feminine hygiene pads, and panty liners.

8. The disposable absorbent article according to claim 1 wherein said substrate has been treated with a high-energy surface treatment.

9. The disposable absorbent article according to claim 8 wherein said high-energy surface treatment is selected from the group consisting of corona discharge treatment, plasma treatment, UV radiation, ion beam treatment, electron beam treatment and combinations thereof.

10. A process for making a disposable absorbent article comprising an absorbent core, said absorbent core comprising a durable, hydrophilic fluid pervious acquisition layer, said process comprising:
    coating an acquisition layer substrate with a hydrophilicity boosting composition, said hydrophilicity boosting composition comprising a surfactant and a hydrophilicity boosting amount of nanoparticles, wherein said nanoparticles have a particle size of from about 1 to about 750 nanometers and wherein the surfactant is present in an amount to facilitate dispersion of the nanoparticles onto the substrate.

11. The process for making a disposable absorbent article according to claim 10 wherein prior to or concurrent with coating of said substrate, said substrate is treated with a high energy surface treatment selected from the group consisting of corona discharge treatment, plasma treatment, UV radiation, ion beam treatment, electron beam treatment and combinations thereof.

12. The process for making a disposable absorbent article according to claim 10 wherein said hydrophilicity boosting composition further comprises a carrier.

13. The process for making a disposable absorbent article according to claim 10 wherein said nanoparticles are inorganic nanoparticles.

14. The process for making a disposable absorbent article according to claim 10 wherein said disposable absorbent article is selected from the group consisting of diapers, adult incontinence products, training pant, feminine hygiene pads, and panty liners.

* * * * *